United States Patent [19]

Sherlock

[11] Patent Number: 4,838,872
[45] Date of Patent: Jun. 13, 1989

[54] BLOOD COLLECTION DEVICE

[75] Inventor: Paul Sherlock, San Francisco, Calif.

[73] Assignee: Sherwood Medical Company, St. Louis, Mo.

[21] Appl. No.: 14,513

[22] Filed: Feb. 13, 1987

[51] Int. Cl.$^4$ .............................................. A61M 1/00
[52] U.S. Cl. .................................. 604/319; 604/321; 604/4
[58] Field of Search ..................... 604/4, 7, 118, 319, 604/321, 322, 403, 408, 134

[56] References Cited

U.S. PATENT DOCUMENTS

| | | | |
|---|---|---|---|
| 3,473,532 | 10/1969 | Eisenberg | 128/227 |
| 3,557,786 | 1/1971 | Barr, Sr. et al. | 128/214 |
| 3,734,154 | 5/1973 | Polk | 604/322 |
| 4,006,745 | 2/1977 | Sorenson et al. | 128/214 R |
| 4,161,179 | 7/1979 | Abramson | 604/134 |
| 4,372,336 | 2/1983 | Cornell et al. | 604/321 |
| 4,429,693 | 2/1984 | Blake et al. | 604/319 |
| 4,443,220 | 4/1984 | Hauer et al. | 604/319 |
| 4,540,413 | 9/1985 | Russo | 604/320 |
| 4,583,972 | 4/1986 | Hunter, III et al. | 604/133 |

FOREIGN PATENT DOCUMENTS 2330101  1/1975  Fed. Rep. of Germany ...... 604/408
1049763 12/1953  France ................................ 604/134

OTHER PUBLICATIONS

Journal of Thoracic and Cardiovascular Surgery, advertisement for Pleur-Evac., vol. 93, No. 2, Feb. 1987.

*Primary Examiner*—C. Fred Rosenbaum
*Assistant Examiner*—Gene B. Kartchner
*Attorney, Agent, or Firm*—Stanley N. Garber; Andrew J. Beck; William R. O'Meara

[57] ABSTRACT

An autotransfusion device for a chest drainage unit is provided that includes a collapsible blood collection and reinfusion bag assembly that includes a collapsible bag with pliable walls and stiffener members, and a holder which receives the assembly. The holder maintains compressive forces on the sides of the stiffener members so they bow outwardly and, in turn, maintain the bag assembly in an expanded conditions for collecting blood while suction is applied to the bag during drainage operations. The collapsible bag assembly can be removed from the holder for reinfusion of the collected blood.

21 Claims, 3 Drawing Sheets

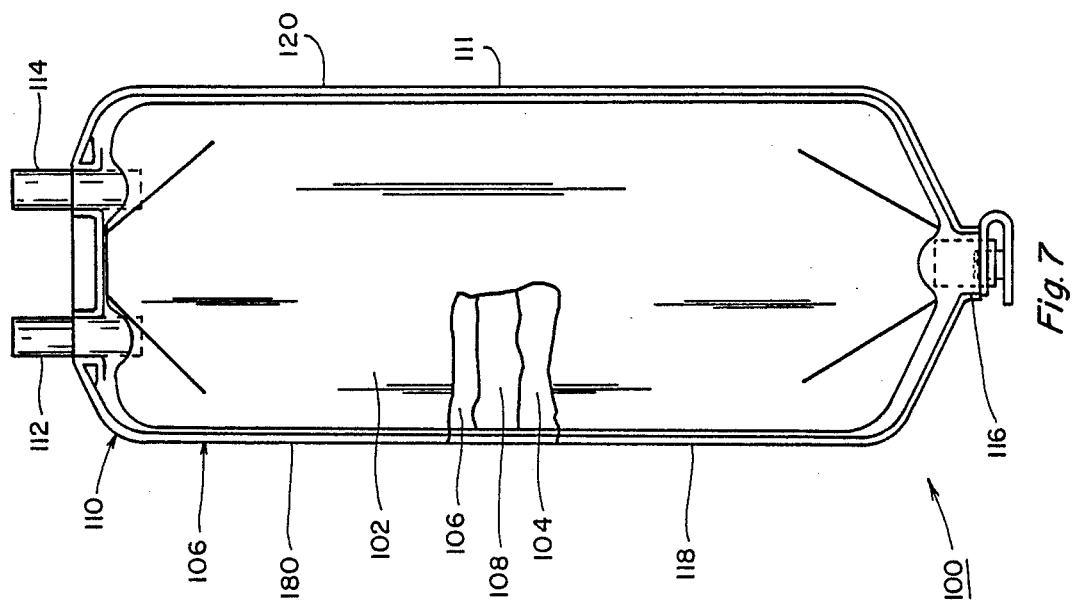
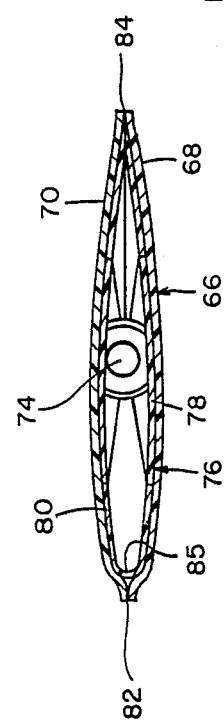
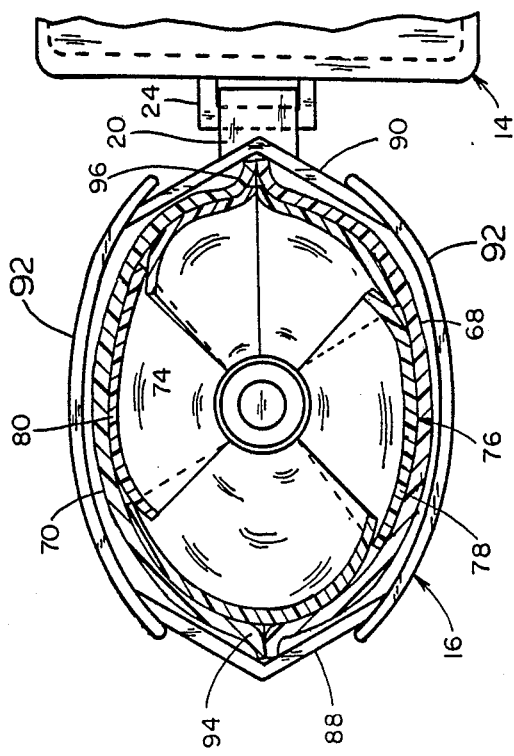

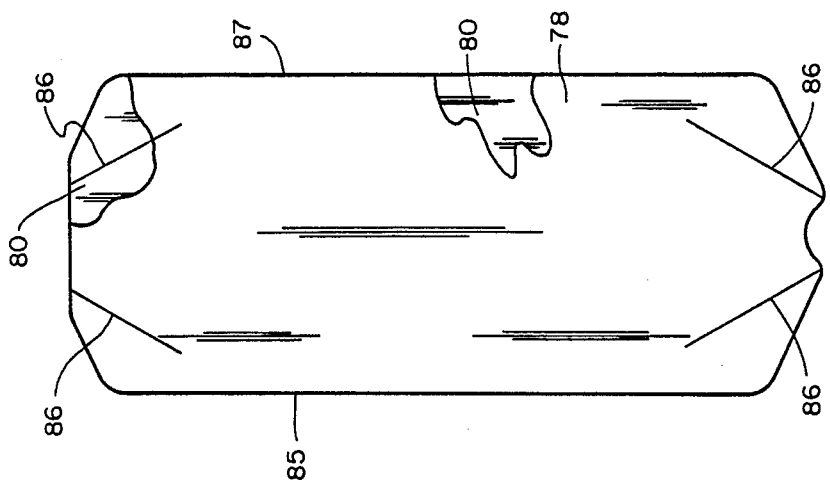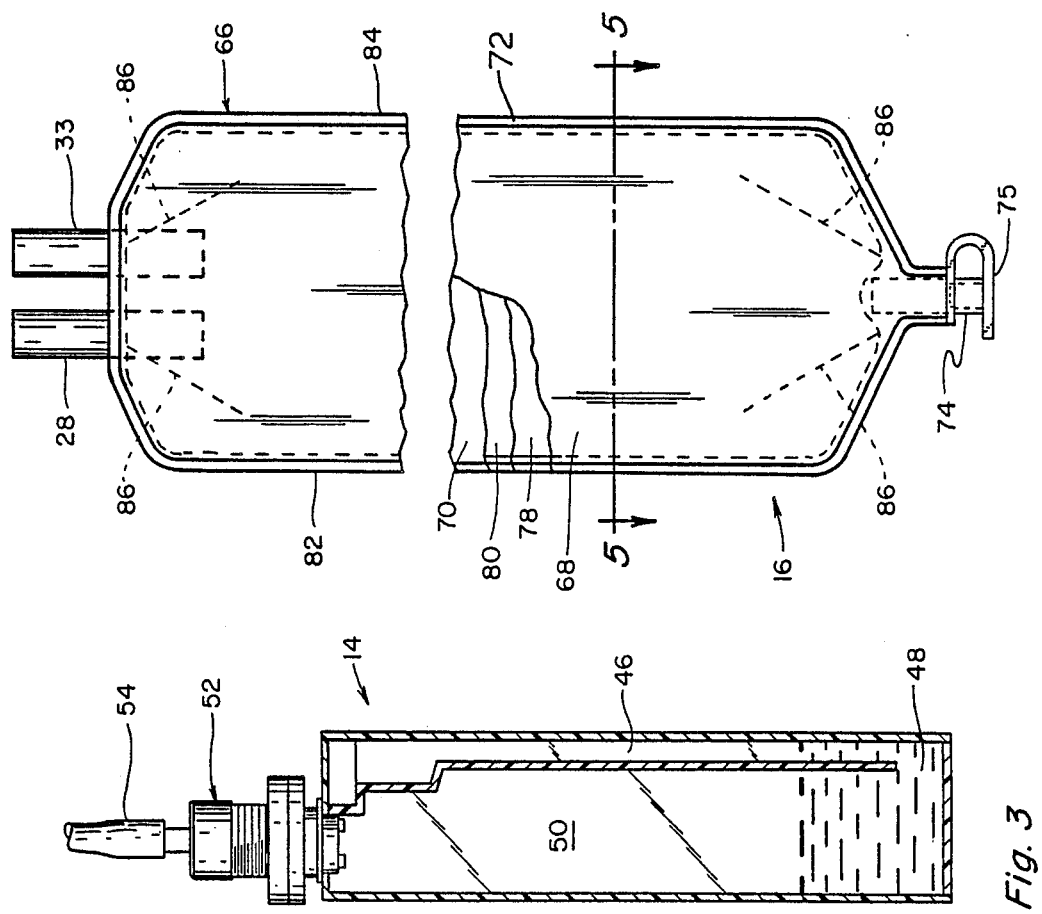

BLOOD COLLECTION DEVICE

TECHNICAL FIELD

This invention relates to blood collection devices, and more particularly to autotransfusion blood collection devices.

BACKGROUND

It is often desirable during surgery, to collect blood from the patient and subsequently return the collected blood to the same patient. Returning the patient's own blood eliminates or reduces the need for supplying the patient with blood from another person and therefore reduces the danger of transmitting a disease to the patient.

After lung surgery, for example, suction is generally applied to the pleural cavity of the patient by means of a catheter connected to a thoracic or chest drainage unit. Blood and gas flow into the drainage unit during the healing process. The collected blood and drainage unit are eventually discarded. If the patient requires blood, stored blood generally from another person must be infused into the patient.

More recently, auxiliary autotransfusion blood collection containers have been employed with chest drainage units which permit reinfusion of the collected blood.

In one case, a blood collection bottle which is non-collapsible is connected to a chest drainage unit such that suction is applied through the bottle to the patient. After the bottle is filled with drainage blood it is used to reinfuse the patient. There are, however, certain problems or disadvantages associated with rigid or non-collapsible autotransfusion bottles. For example, during reinfusion the rigid bottle must be vented to atmosphere to allow the collected blood to flow from it to the patient. Thus, air is in contact with the blood and may affect the blood characteristics. Special care must be taken to avoid infusion of air into the patient during reinfusion. Also, an air filter at the vent must be used to avoid possible air-borne contaminants.

In another arrangement, an auxiliary blood collection device includes a pliable bag having an outer sleeve. The bag is held in an open or expanded condition by a stent or holder having rigid wire arms extending between the bag and sleeve to maintain the bag open for receiving drainage blood against the suction forces during operation of the chest drainage unit. After the bag is filled, it can be removed from the holder and employed to reinfuse the patient with the collected blood. One problem associated with this arrangement is that the volume of the pliable bag generally varies to a significant extent with different suction forces because the walls of the bag tend to move inwardly, especially at locations between the holder arms. Thus, the indicated amount of blood collected may be inaccurate where the operating suction force or negative pressure in the bag differs from a predetermined value.

SUMMARY OF THE INVENTION

It is therefore an object of the present invention to provide an improved blood collection device which permits the collection and reinfusion of the collected blood into the patient.

Another object is to provide an improved autotransfusion blood collection device well suited for connection with a chest drainage unit wherein blood collected from the patient can be readily reinfused into the patient in a safe and efficient manner.

Still another object is to provide an improved chest drainage apparatus which includes a blood collection bag assembly that is rigid when under negative pressure during drainage collection and which is compressible during reinfusion to allow blood flow without air venting.

Another object is to provide a blood collection bag assembly which can be shipped and stored in a flattened condition, and expanded to an approximate cylindrical shape for use in collecting blood.

In accordance with one form of the present invention, a blood collection device is provided which includes a pliable bag having an inlet for connection with a source of blood, and a pair of members of stiffer material than that of the bag disposed respectively in facing relation adjacent the opposed walls of the bag. The members are flexible to expand the pliable bag in response to compressive forces applied to the members.

In accordance with another aspect of the invention a blood collection device is provided which includes a pliable blood collection bag having relatively stiff flexible members, and a holder for receiving the bag for maintaining compressive forces on opposed sides of the flexible members to maintain the bag expanded in an approximate cylindrical shape.

In accordance with still another aspect, a chest drainage apparatus is provided which includes a chamber connectable to a source of suction, and an autotransfusion device. The device includes a pliable blood collection bag having an inlet for receiving blood from a patient and a fluid outlet for fluid communication with the chamber, a pair of relatively stiff flexible members adjacent opposed walls of the bag, and a holder adapted to receive the bag and members and to maintain compressive forces on the members for maintaining the bag expanded.

These as well as other objects and advantages of the present invention will become apparent from the following detailed description and accompanying drawings.

BRIEF DESCRIPTION OF THE DRAWINGS

FIG. 2 is a cross-sectional view taken along the line 2—2 of FIG. 1;

FIG. 3 is a cross-sectional view taken along line 3—3 of FIG. 1;

FIG. 4 is an elevational view of the autotransfusion bag assembly of FIG. 1 but in its unrestrained or free state condition;

FIG. 5 is a cross-sectional view taken along the line 5—5 of FIG. 4

FIG. 6 is an elevational view of the bag stiffening member of FIG. 1 but in its unrestrained or free state condition; and FIG. 7 is a side elevational view of autotransfusion bag assembly in accordance with a modified embodiment of the present invention.

DESCRIPTION OF THE PREFERRED EMBODIMENT

Figure 1:
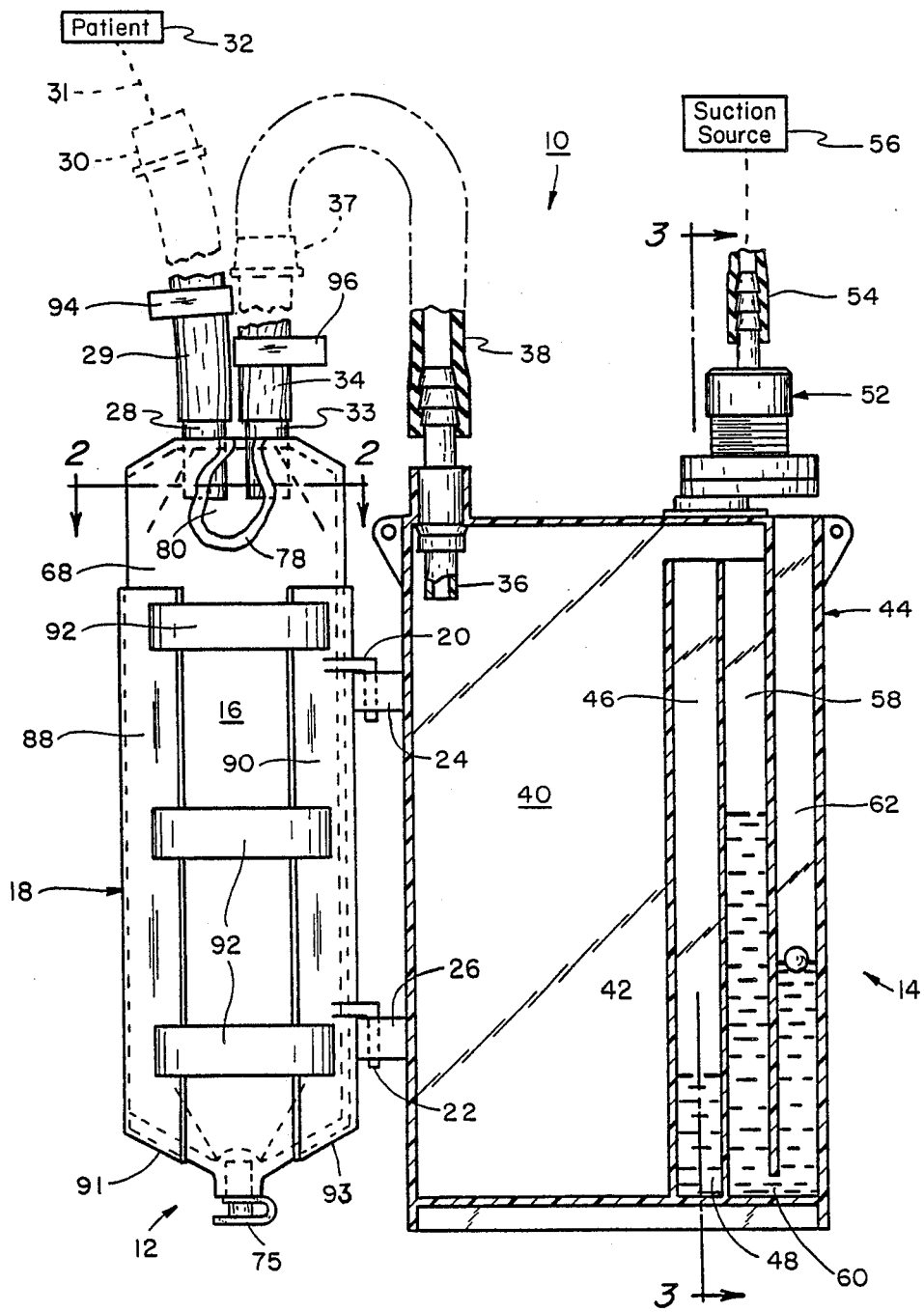
FIG. 1 is a elevational view, partly in section, of a chest drainage system in accordance with a preferred embodiment of the present invention.

Referring now to the drawings, a chest drainage system 10 is shown including autotransfusion blood collection device 12 connected to the side of a chest drainage unit 14. The device 12 includes an autotransfusion or blood collection and reinfusion bag assembly 16 and a bag expanding member or holder 18 receiving the bag assembly 16. As shown for illustration, the holder 18 has a pair of integral depending lugs 20 and 22 respectively received in a pair of brackets 24 and 26 integrally connected to the chest drainage unit 14 whereby the device 12 is removably connected to the unit 14.

As seen in FIG. 2, the holder 18 maintains the bag assembly 16 in an expanded condition for receiving body fluids from the patient, as will be further explained hereafter. The bag assembly 16 has a fluid inlet 28 at the top of the assembly connected to a flexible tube 29. Tube 29 is shown connected by a tube connector 30 to a suction catheter 31 that has its distal end inserted into the pleural cavity of a patient indicated at 32, the connector and catheter being illustrated in phantom. Body fluid such as air or gas and blood flow from the patient into the bag assembly 16 during operation of the system 10.

The bag assembly 16 also includes a gas outlet 33 at the top of the assembly that is connected to a flexible tube 34 which, in turn, is connected to a chest drainage inlet 36 through a tube connector 37 and flexible tube 38.

The chest drainage unit 14 is shown for illustration including a fluid collection chamber 40, an underwater seal chamber indicated generally at 42, and a liquid monometer indicated at 44. The liquid underwater seal includes a relatively narrow vertical channel 46 open at the top where it is in fluid communication with the collection chamber 40. Channel 46 has an opening 48 at the bottom which communicates with a relatively large gas oulet chamber 50 of the water seal 42, as seen in FIG. 3. Connected to the top of outlet chamber 50 is a suction regulator 52 that is connected by a flexible tube 54 to a source of suction 56 (FIG. 1) which may be a conventional hospital wall suction source. The liquid monometer includes a vertical channel 58 connected in fluid communication with collection chamber 40 at the top and by a passage 60 at the bottom to a second vertical column 62 that is open at the top to the atmosphere. Both the underwater seal 42 and the liquid monometer 45 are shown provided with quantities of liquid or water.

When a partial vacuum or negative pressure exists in the underwater seal chamber 50 (FIG. 3), any air or gas from the patient flows from catheter 31 into the upper portion of bag assembly 16, into outlet 33, into collection chamber 40, downwardly into the water in water seal channel 46, through the bottom opening 48, upwardly through the water in outlet chamber 50 and then to the suction source 56. The underwater seal 42 prevents any atmospheric air from flowing through the unit 14 to the patient. Because the liquid monometer is responsive to the pressure in collection chamber 40, the level of liquid in the liquid monometer 44 will vary in height providing an indication of the suction level or negative pressure in the collection chamber and therefore in the pleural cavity of the patient. The construction and operation of the chest drainage unit 14 including the section regulator 52 are shown and described in detail in U.S. Pat. No. 4,372,336 and are hereby incorporated herein by reference.

The collection and reinfusion bag assembly 16, shown also in its unrestrained or free condition in FIGS. 4 and 5, includes a collapsible pliable bag 66 formed of a pair of opposed piable walls or sheet members 68 and 70 disposed in parallel facing relation and connected together, for example, by heat sealing to effect a peripheral seal indicated at 72. The peripheral seal at 72 extends around the tubular inlet 28 and tubular gas outlet 33 to seal them to the bag 66. Also, the seal 72 extends around and seals a tubular blood outlet 74 at the bottom of the bag 62. A closure plug 75 integrally tethered to the bag normally maintains the outlet 74 closed.

The bag assembly 16 also includes a resilient bag stiffener indicated generally at 76 which maintains the pliable bag 66 in an expanded condition when the assembly 16 is in the holder 18. The stiffener 76, which is shown also in its unrestrained or free condition in FIGS. 5 and 6, is formed of a pair of parallel facing sheet members or panels 78 and 80 shown, for example, integrally connected at one side 82 and secured together such as by an adhesive or heat seal at the opposite side 84. Stiffener members 78 and 80 are made of a flexible but relatively rigid plastic, they being preferably substantially more rigid and resilient than the walls 68 and 70 of bag 66. For example, the bag 66 may be formed of a pliable plastic such as a pliable polyvinyl chloride while the more rigid stiffener members 78 and 80 may be formed of a flexible, more resilient and rigid plastic such as polyetrylene terephthalate (PET-C) sheet material.

While the stiffener members 78 and 80 may be discrete sheets they are shown within bag 66 as integrally connected at the left side 82, the left side serving as a hinge. Stiffener members 78 and 80 may be cut from sheet stock or molded in sheet form. The stiffener 76 may be folded at the left side and seamed such that there is a slight outwardly bowing of each stiffener members as shown in FIG. 5. This outward bowing facilitates proper bending of the stiffener members to produce an expanded or rounded bag assembly (FIG. 2) when compressive forces are applied t the assembly 16 at the opposed sides 82 and 84, as will be further discussed herein. Also, each of the members 78 and 80 is provided as its upper and lower ends with a pair of slits or slots 86 that extend through the wall of the members. While the slots 86 may be vertical each pair of slots 86 at each end of each of the member 78 and 80 is shown to diverge as they extend toward the interior of the member from the end edge of the member, the slots of each pair being closest to each other where they intersect the periphery or end edge of the member. The slots 86 allow adjacent portions of the stiffener members to move past each other (FIG. 2) tending to allow the bag 66 to generally become tapered at the top of the bag and generally conical at the bottom when the opposed sides 85 and 87 of the stiffener 76 are urged tward each other when compressive forces are applied to the opposed sides 82 and 84 of the bag assembly 16. The slots 86 may be straight and still aid in allowing the opposed ends of the bag assembly to take a satisfactory shape. The side edges 82 and 84 of the bag are respectively adjacent side edges 85 and 87 of the stiffener 76.

The holder 18 may be various constructions, such that it will hold the collection and reinfusion bag assembly 16 in an open or expanded condition such as illustrated in FIGS. 1 and 2 after the assembly is inserted into the holder 18. The holder 18 is shown for illustration of FIGS. 1 and 2 including a pair of opposed rigid vertical sidewalls or members 88 and 90 secured together by connecting struts 92 and maintained in predetermined spaced relation from each other. As best seen in FIG. 2, the members 88 and 90 are V-shaped and the lateral distance between the inside corners of these members is less than the width of the bag assembly 16 including the width of the stiffener member 76. That is, the distance between the inside corners of the holder members is less than the distance between the side edges 82 and 84 of bag assembly 16, when in the uncompressed or generally flattened state as in FIGS. 4 and 5. In this way, when clamping or compressive forces are applied to the opposite sides 82 and 84 of the assembly 16 compressive forces are applied to side edges 85 and 87 of the stiffener members 78 and 80 so that central portions of members 78 and 80 bulge or bow outwardly causing the pliable walls 68 and 70 of bag 66 to follow and expand to the condition shown in FIGS. 1 and 2.

When inserting bag assembly 16 into the holders 18, opposed clamping or compressive forces are applied to sides 82 and 84 urging these sides toward each other as well as sides 85 and 87 of the stiffener 76 together, the stiffener members 78 and 80 oppositely bow or bulge and expand the bag assembly 16 including bag 66. While in the expanded condition, the bag assembly 16 is inserted into the upper open end of holder 18 with the opposed sides 82 and 84 of the bag assembly received in the inside corners of the V-shaped holder members 88 and 90 for proper orientation of the bag 66 and holder. The bag assembly 16 is slid downwardly until it engages a bottom walls 91 and 93 (FIG. 1) of the holder 18. Since the holder members 88 and 90 are spaced from each a distance less than the normal or free width of the bag assembly 16 (FIG. 4), the bag 16 is held open by the holder. The bag assembly 16 is held in an approximately cylindrical shape in the holder 18 which shape provides the greatest resistance to collapse from negative pressure and provides a desired volume for blood collection.

With the autotransfusion device 12 connected and arranged as shown in FIG. 1, gas or air from the patient flows through tube 30 into the expanded bas assembly 66 whereby blood flows toward the bottom of the bag assembly while suction applied through the chest drainage unit by the suction source 56 causes the gas from the patient to flow through the gas outlet 33 tube 38, into the collection chamber 40 of the chest drainage unit 14 by way of inlet 36, through the water seal 42 including channel 46 and chamber 50 and to the suction source by way of the suction regulator 52. Thus, the blood and gas from the patient are separated, the blood filling the bag 66 and gas being removed by the chest drainage unit. Should the bag assembly 66 become overfilled with blood, blood will then overflow into the collection chamber 40 by way of gas outlet 33 and tube 38. Preferably, the autotransfusion device 12 is removed from the patient and chest drainage unit prior to it becoming completely filled. Upon removal, a new autotransfusion bag assembly may be inserted into holder 18 or a new autotransfusion device 12 can be attached to the chest drainage unit 14.

In use, after the autotransfusion bag assembly 16 has been filled with the patient's blood to a desired level, the tubes 29 and 34 may be closed by any conventional or suitable tube clamps such as generally indicated at 94 and 96 in FIG. 1, to allow the catheter 31 and inconnecting tube 38 to be removed from the tube connectors 30 and 37. The bag assembly 16 can then be slid upwardly and out of holder 18 so that blood collected from the patient can be returned to the same patient from which it was collected. The plug 76 can be removed and infusion tubes connected to the liquid or blood outlet 74 for reinfusing the blood into the patient.

Since the bag assembly 16, when removed from holder 18, is collapsible, the bag assembly 16 can conveniently be used in the same or similar manner during infusion as a conventional blood bag. Also, a standard pressure cuff can be used if desired to squeeze the bag 66 where increased blood flow to the patient is desired.

In the modified embodiment shown in FIG. 7, an autotransfusion or collection and reinfusion bag assembly 100 is shown including separate stiffening members, indicated at 102 and 104 that are connected such as by an adhesive to the outer surfaces of a pair of opposed pliable walls 106 and 108 of a pliable bag indicated at 110. The assembly 100 is shown in its unrestrained or free state condition. Stiffening members 102 and 104 may be made of a relatively resilient, flexible plastic. The bag 110, like bag 66, has its opposed walls 106 and 108 connected together around the periphery thereof by a peripheral seal or heat seam 111 which also extends about an inlet 112, gas outlet 114, and a blood outlet 116. When clamping or compressive forces are applied to the opposed sides indicated at 118 and 120, which are adjacent the sides of seam 111, the relatively stiff members 102 and 104 oppositely bow outwardly generally into a configuration somewhat circular in section and in doing so cause the adjacent walls 106 and 108 of the pliable bag to follow, thereby, in effect expanding the pliable bag 101. The expanded bag assembly 100 may then be moved into a suitable holder such as holder 18 in FIG. 1 by which it will be maintained in an expanded condition to receive drainage blood. Bag assembly 100 can be used to reinfuse the patient's blood in the same manner as bag assembly 16.

By employing a pliable blood collection bag having pliable sidewalls or opposed panel members, such as bags 66 or 110, and relatively rigid and flexible opposed sheet or panel members of a stiffener material, the pliable bag is readily maintained in an expanded condition within a holder for efficiently receiving quantities of blood. Conventional blood infusion techniques can be employed when using the autotransfusion bag assemblies 16 and 100.

As various changes could be made in the above described apparatus without departing from the scope of the invention, it is intended that all matter contained in the above description or shown in the drawings shall be interpreted as illustrative and not in a limiting sense.

What is claimed is:

1. A body fluid collection device comprising a collapsible bag having a pair of opposed sidewalls, and an inlet for receiving body fluid, and stiffener means including a pair of relatively stiff flexible members respectively adjacent said sidewalls and having opposed side edges, said members having portions between said side edges bendable outwardly in opposite directions from each other in response to the application of a force external to said bag tending to move said side edges generally toward each other to expand said bag for receiving body fluid through said inlet, and means external to said bag for maintaining a compressive force on said opposed side edges to maintain said bag expanded including a pair of opposed members spaced apart less than the distance between said side edges for receiving said bag and flexible members therebetween.

2. The device of claim 1 wherein each of said relatively stiff flexible members has a pair of slits extending inwardly from an edge thereof adjacent each of the opposite ends thereof to allow said bag to become tapered at the opposite ends thereof when expanded.

3. A body fluid collection device comprising a collapsible bag assembly including a collapsible bag having a pair of opposed sidewalls, an inlet for receiving body fluid, and stiffener means including a pair of relatively stiff flexible members respectively adjacent said sidewalls and have opposed side edges, said members having portions between said side edges bendable outwardly in opposite directions from each other in response to the application of a force tending to move said side edges generally toward each other to expand said bag for receiving body fluid through said inlet, and means for maintaining a compressive force on said opposed side edges to maintain said bag expanded including a holder having a pair of wall adapted to receive said bag assembly therebetween, said wall being spaced apart a distance less than the distance between said opposed side edges to maintain a compressive force on said opposed side edges.

4. The device of claim 3 including a gas outlet connected in fluid communication with the interior of said bag for connection with a suction source to effect suction forces in the interior of said bag, said stiff flexible members being predeterminately rigid so as to prevent collapse of said bag when the interior of said bag is subjected to suction forces.

5. The device of claim 3 wherein said holder includes means for attaching said holder to a chest drainage unit, and means for connecting the interior of said bag in fluid communication with the chest drainage unit to supply suction to the interior of said bag during operation of the chest drainage unit.

6. The device of claim 3 wherein said sidewalls are sealed together adjacent the periphery thereof, said bag having opposed peripheral side edges respectively adjacent said opposed side edges of each of said flexible members, said bag having upper and lower edges spaced a greater distance apart than the distance between said opposed side edges of said bag so that the height of said bag is greater than the width thereof.

7. The device of claim 3 wherein said flexible members are inside said bag.

8. The device of claim 7 wherein said flexible members are of sheet material, and said members are integrally connected together at least along one side thereof.

9. The device of claim 3 wherein said flexible members are respectively fixed to the outer surfaces of said opposed sidewalls.

10. The device of claim 9 wherein said flexible members are respective sheets of plastic.

11. An autotransfusion device comprising a blood collection and reinfusion member comprising a collapsible bag including a pair of opposed pliable sidewalls, an inlet at the top for receiving body fluid including blood from a patient, and a blood outlet at the bottom for discharging blood from said bag during reinfusion, bag stiffener means including a pair of flexible members respectively engaging said sidewalls and having portions bendable outwardly away from each other in response to compressive forces applied to a pair of opposed side edges of said flexible members to move portions of said bag sidewalls in opposite directions to thereby expand said bag for receiving body fluid, and a holder for receiving said blood collection and reinfusion members, said holder having opposed walls predeterminately spaced apart to maintain a compressive force applied to said pair of opposed side edges to maintain said bag in an expanded condition.

12. The device of claim 11 wherein said bag further includes a gas outlet at the top end thereof communicating with the interior of said bag, and means for connecting said gas outlet to a source of suction.

13. The device of claim 11 wherein said bag includes a gas outlet at the top end thereof, and means for connecting said outlet to a chest drainage unit for applying a negative pressure to the interior of said bag.

14. The device of claim 13 further including means for connecting said holder to a chest drainage unit.

15. The device of claim 11 wherein said sidewalls comprise a pair of pliable plastic sheet members sealed together along portions of the top ends and along the sides thereof, said flexible members comprise a pair of flexible plastic sheet members of stiffer material than said pliable sheet members respectively fixed to the outer surfaces of said pliable plastic sheet members.

16. The device of claim 15 wherein the material of each of said sheet members is substantially less flexible and more resilient than that of each of said bag sidewalls.

17. The device of claim 16 wherein said bag consists of only two sheet members and said holder consists of only two flexible sheet members.

18. A chest drainage device comprising a chest drainage unit including a collection chamber, an underwater seal chamber, means for connecting a source of suction to said collection chamber through said underwater seal chamber, and an autotransfusion device including a blood collection and reinfusion member, said member including a collapsible bag having a pair of pliable sheet members connected together along the upper and lower ends and the opposed sides of the bag, an inlet connected at the upper end of said bag and adapted for connection in fluid communication with the plueral cavity of a patient for allowing fluid to flow into said bag from the plueral cavity of the patient, a gas outlet connected to the upper end of said bag, means for connecting said gas outlet in fluid communication with said collection chamber, and a blood outlet at the bottom of said bag for infusing blood collected in the bag into the patient, stiffener means including a pair of flexible sheet members respectively engaging said pliable sheet members and each being of a material which is stiffer than that of each of said pliable sheet members, said flexible sheet members having upper and lower ends respectively adjacent said upper and lower ends of said bag, said flexible sheet members having opposed sides respectively adjacent said opposed sides of said bag, and a holder for receiving said blood collection and reinfusion member, said holder having a pair of opposed walls predeterminately spaced to apply a compressive force on the opposed sides of said flexible sheet members to maintain a portion of said sheet members bowed outwardly from each other to thereby bow said pliable sheet members of said bag outwardly from each other to maintain said bag expanded in a substantially cylindrical shape for receiving blood from the plueral cavity of the patient.

19. The device of claim 18 further including means for releasably connecting said holder to said chest drainage unit, and means for releasably closing said blood outlet, and said flexible sheet members are resilient.

20. The device of claim 18 wherein said flexible sheet members are respectively fixed to the outer surfaces of said pliable sheet members.

21. The device of 20 wherein all of said sheet members are of plastic materials, and each of said flexible sheet members have first and second pairs of slits extending respectively frm the upper and lower edges thereof.

* * * * *